United States Patent
Jang et al.

(10) Patent No.: US 11,491,195 B2
(45) Date of Patent: *Nov. 8, 2022

(54) **COMPOSITION COMPRISING *LACTOBACILLUS PLANTARUM* CJLP475 STRAIN AND *LACTOBACILLUS PLANTARUM* CJLP17 STRAIN AND USE THEREOF**

(71) Applicant: CJ CHEILJEDANG CORPORATION, Seoul (KR)

(72) Inventors: Yoon Tack Jang, Seoul (KR); Hee-Yeon Kim, Seoul (KR); Ho Jin Moon, Seoul (KR); Seo Hyung Woo, Seoul (KR); Kyung Min Lee, Seoul (KR); Sung Hun Kim, Seoul (KR); Gi Duk Bae, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/619,050

(22) PCT Filed: Jul. 12, 2019

(86) PCT No.: PCT/KR2019/008677
§ 371 (c)(1),
(2) Date: Dec. 3, 2019

(87) PCT Pub. No.: WO2020/013670
PCT Pub. Date: Jan. 16, 2020

(65) Prior Publication Data
US 2021/0401903 A1 Dec. 30, 2021

(30) Foreign Application Priority Data
Jul. 13, 2018 (KR) .................. 10-2018-0081909

(51) Int. Cl.
| | |
|---|---|
| *A61K 35/747* | (2015.01) |
| *A23K 10/18* | (2016.01) |
| *A23L 33/135* | (2016.01) |
| *C12R 1/25* | (2006.01) |
| *A61P 31/14* | (2006.01) |
| *C12N 1/20* | (2006.01) |
| *A23K 50/30* | (2016.01) |

(52) U.S. Cl.
CPC ............ *A61K 35/747* (2013.01); *A23K 10/18* (2016.05); *A23L 33/135* (2016.08); *A61P 31/14* (2018.01); *C12N 1/205* (2021.05); *A23K 50/30* (2016.05); *A23Y 2220/67* (2013.01); *C12R 2001/25* (2021.05)

(58) Field of Classification Search
CPC ..... A61K 35/747; A23K 10/18; A23L 33/135; C12N 1/205; C12R 2001/25
See application file for complete search history.

(56) References Cited

U.S. PATENT DOCUMENTS

| | | |
|---|---|---|
| 9,572,845 B2 | 2/2017 | Kim et al. |
| 9,572,846 B2 | 2/2017 | Kim et al. |
| 10,093,995 B2 | 10/2018 | Kim et al. |
| 10,130,666 B2 | 11/2018 | Kim et al. |
| 2011/0020395 A1 | 1/2011 | Benyacoub et al. |

FOREIGN PATENT DOCUMENTS

| | | |
|---|---|---|
| CN | 108102959 A | 6/2018 |
| KR | 2003-0063961 A | 7/2003 |
| KR | 10-2010-0063503 | 6/2010 |
| KR | 10-2011-0000854 A | 1/2011 |
| KR | 10-2011-0046020 | 5/2011 |
| KR | 2012-0064416 A | 6/2012 |
| KR | 10-2012-0111608 A | 10/2012 |
| KR | 10-2013-0056264 | 5/2013 |
| KR | 10-2015-0044764 | 4/2015 |
| KR | 10-2017-0009458 A | 1/2017 |
| KR | 10-2017-0072825 | 6/2017 |
| KR | 10-2019-0063795 A | 6/2019 |

OTHER PUBLICATIONS

Gisela et al. "Enhacement of the Viability of Lactobacillus plantarum during the Preservation and Storage Process Based on the Response Surface Methodology", Food and Nutrition Sciences, 2014, 5, 1746-1755 (Year: 2014).*
U.S Appl. No. 16/619,804; U.S Appl. No. 16/618,745, filed 2019.*
U.S Appl. No. 16/979,725, filed 2020.*
Lee et al., "Effect of *Lactobacillus plantarum* CJLP243 on the growth performance and cytokine response of weaning pigs challenged with enterotoxigenic *Escherichia coli*," *J. Anim. Sci.* 90:3109-3717 (2012).
Lee et al., "The Effect of *Lactobacillus plantarum* CLP-1 on the Swine Viruses," *Korean Society for Biotechnology and Bioengineering Journal* 26:62-68 (2011) (w/English Abstract).
Lee et al., "Differential Cytokine Regulatory Effect of Three *Lactobacillus* Strains Isolated from Fermented Foods," *J. Microbiol. Biotechnol.* 26(9):1517-1526 (2016).
Sirichokchatchawan et al., "Protective Effects of Cell-Free Supernatant and Live Lactic Acid Bacteria Isolated from Thai Pigs Against a Pandemic Strain of Porcine Epidemic Diarrhea Virus," *Probiotics & Antimicro. Prot.* 10:383-390 (2018).
U.S Appl. No. 16/618,745, filed Dec. 2, 2019, *Lactobacillus plantarum* CJLP475 Strain Having Antiviral and Immunomodulatory Effects and Composition Comprising the Same.
Pensaert et al., "A New Coronavirus-Like Particle Associated With Diarrhea in Swine," Archives of Virology 58:243-247 (1978).

(Continued)

*Primary Examiner* — Ruth A Davis
(74) *Attorney, Agent, or Firm* — Seed IP Law Group LLP

(57) ABSTRACT

The present disclosure relates to a composition comprising a *Lactobacillus plantarum* CJLP475 strain deposited under Accession No. KCCM12287P; and a *Lactobacillus plantarum* CJLP17 strain deposited under Accession No. KCCM12249P, and use thereof.

13 Claims, 6 Drawing Sheets

Specification includes a Sequence Listing.

(56) References Cited

OTHER PUBLICATIONS

Shintawati et al., "Lactobacillus plantarum modulatory Effect on the Secretion of Interleukin-10,TGFB, and Fibronectin in Macrophages and Skin Dermal Fibroblasts Culture," International Journal of Science and Research (IJSR) ISSN (Online):2319-7064 Index Copernicus Value (2015):78,96 | Impact Factor (2015):6.391 (6 pages).

Song et al., "Porcine epidemic diarrhoea virus: a comprehensive review of molecular epidemiology, diagnosis, and vaccines," Virus Genes 44:167-175 (2012).

Boricha et al., "In vitro evaluation of probiotic properties of Lactobacillus species of food and human origin," *LWT—Food Science and Technology* 106:201-208 (2019).

\* cited by examiner

[FIG. 1]
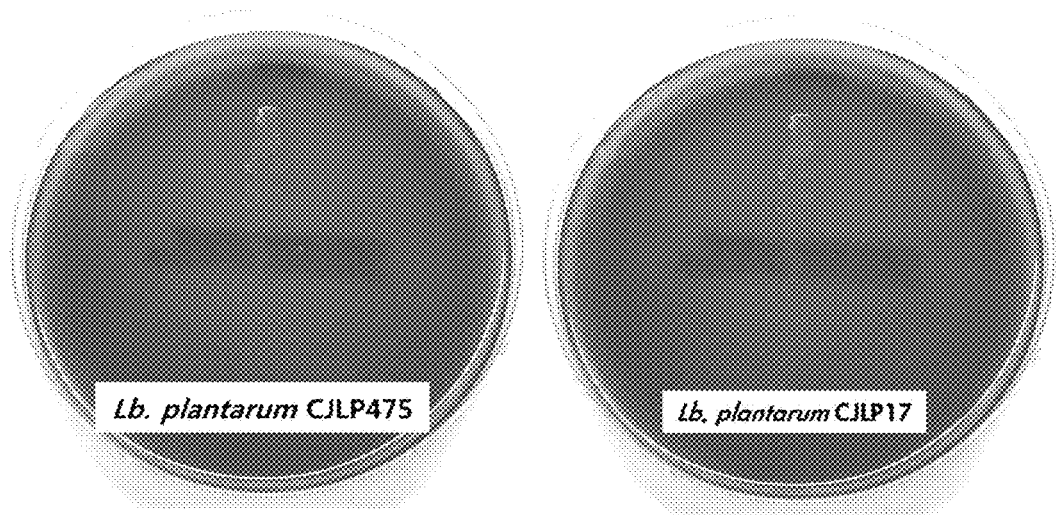
[FIG. 2]
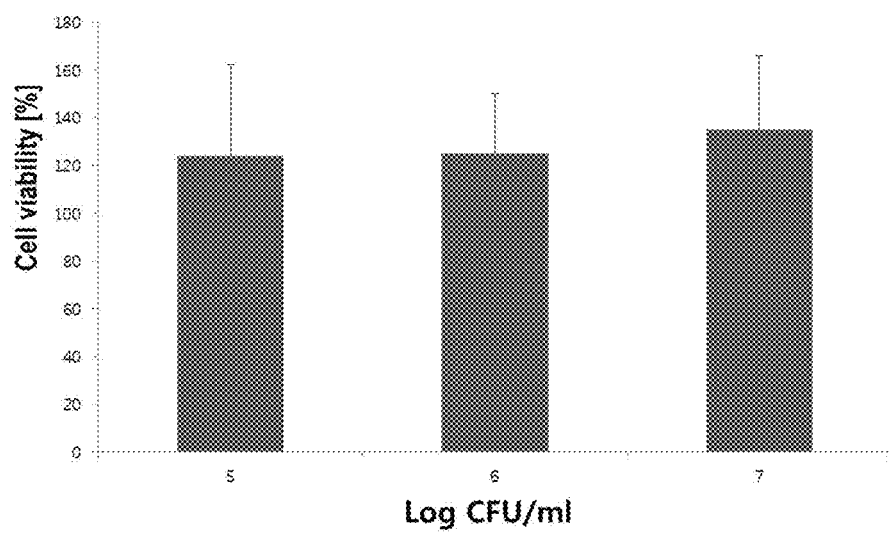

[FIG. 3]
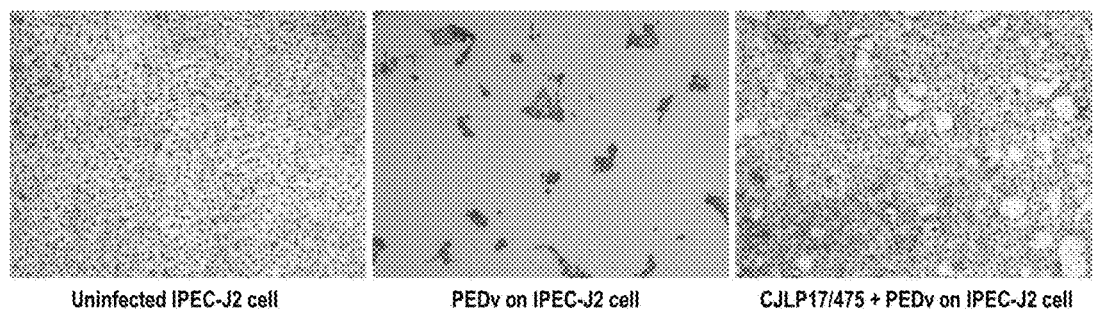
Uninfected IPEC-J2 cell    PEDv on IPEC-J2 cell    CJLP17/475 + PEDv on IPEC-J2 cell
[FIG. 4]
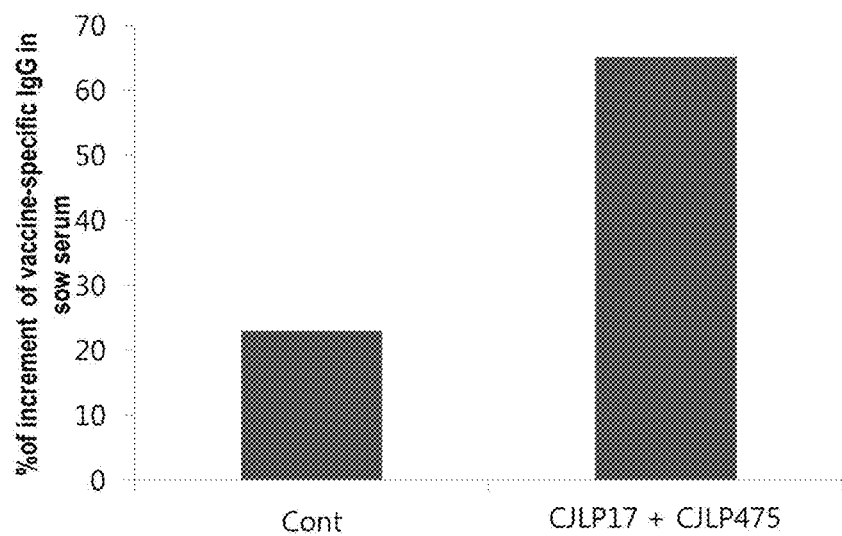

[FIG. 5]
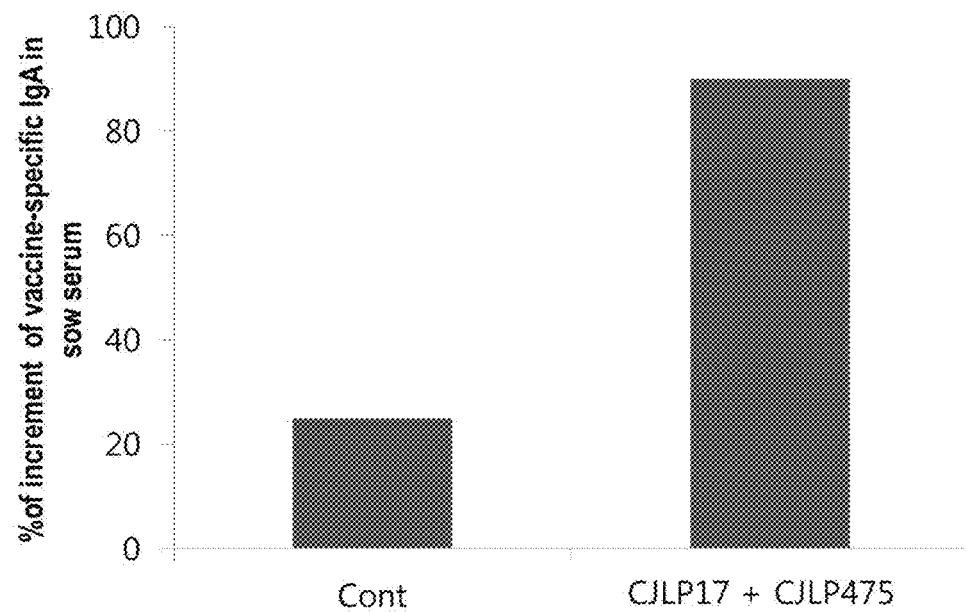
[FIG. 6]
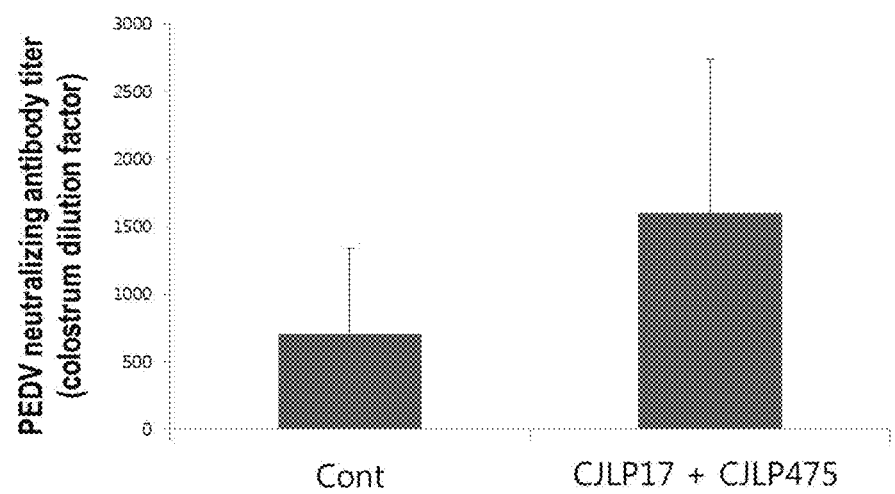

[FIG. 7]
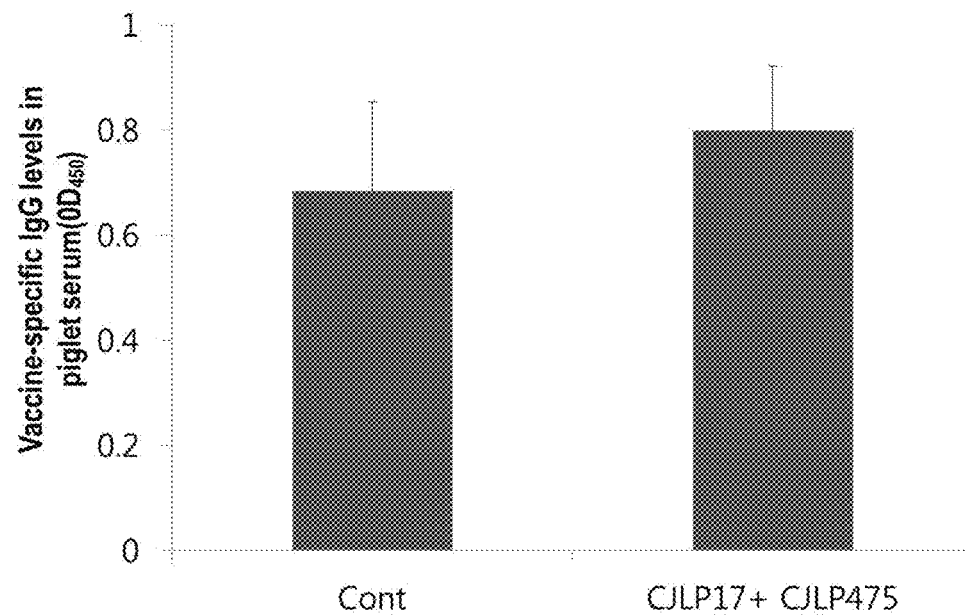
[FIG. 8]
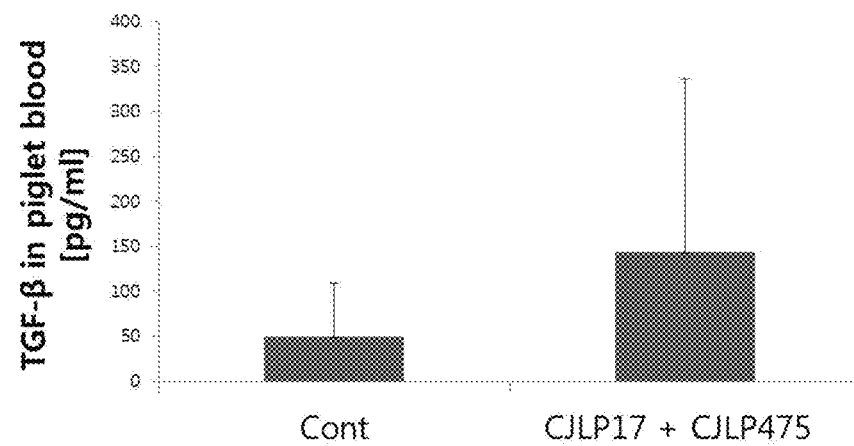

[FIG. 9]
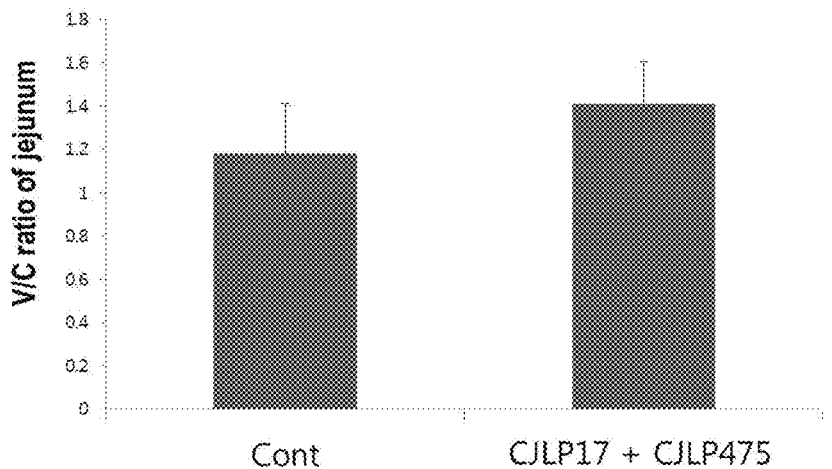
[FIG. 10]
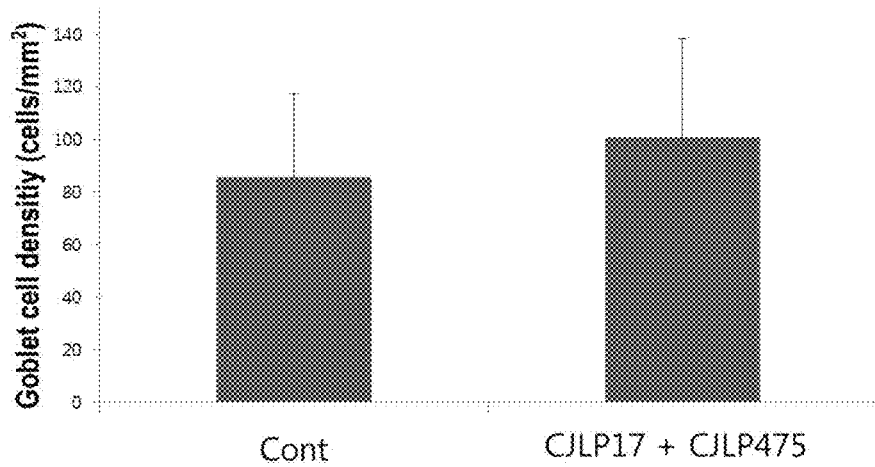
[FIG. 11]
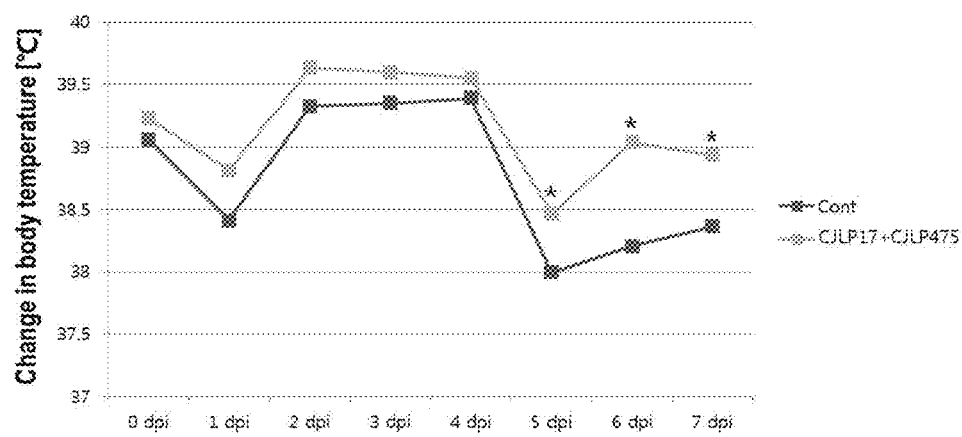

[FIG. 12]
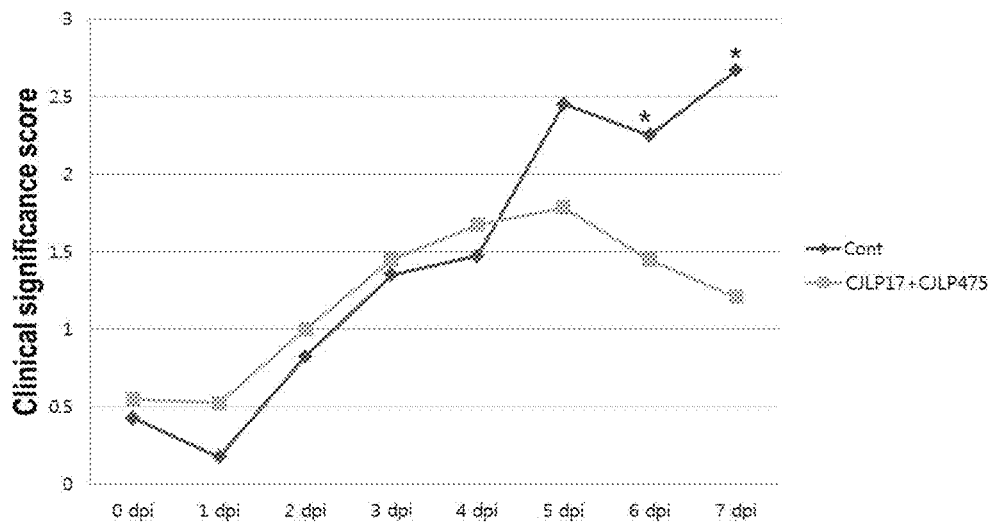
[FIG. 13]
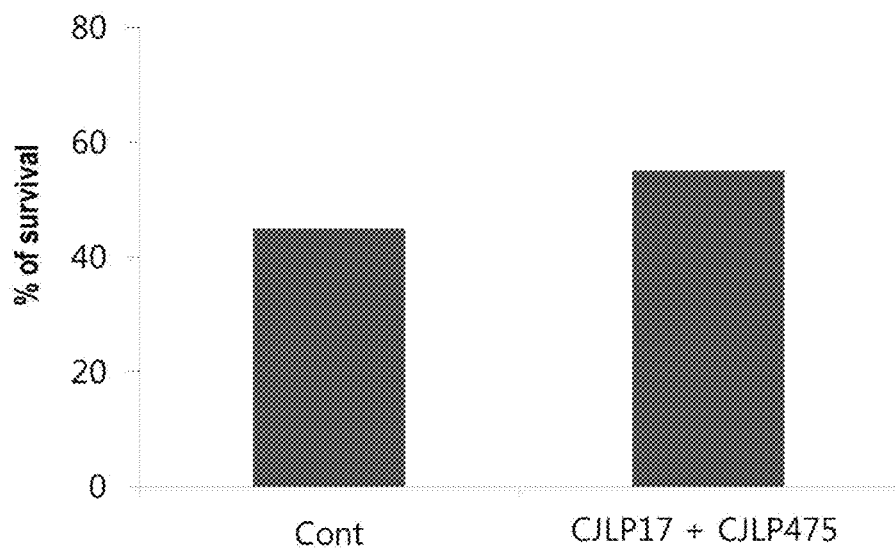

COMPOSITION COMPRISING *LACTOBACILLUS PLANTARUM* CJLP475 STRAIN AND *LACTOBACILLUS PLANTARUM* CJLP17 STRAIN AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_457USPC_SEQUENCE LISTING.txt. The text file is 4.3 KB, was created on Nov. 25, 2019, and is being submitted electronically via EFS-Web.

TECHNICAL FIELD

The present disclosure relates to a composition including a *Lactobacillus plantarum* CJLP475 strain and a *Lactobacillus plantarum* CJLP17 strain, which have acid-resistance, bile-resistance, and antiviral and immune-enhancing activities.

BACKGROUND ART

In the current livestock industry, livestock are killed due to highly contagious viral diseases, and this often leads to economic damage to farms. In particular, in the swine industry, infectious diseases caused by viruses and germs, such as porcine respiratory disease complex, postweaning multisystemic wasting syndrome, porcine reproductive and respiratory syndrome, porcine epidemic diarrhea, which are the four major chronic wasting diseases, have caused huge economic losses.

Among them, porcine epidemic diarrhea is a porcine digestive disease caused by the infection of porcine epidemic diarrhea virus (PEDV), a member of the corona virus family. The virus proliferates in the villi of the small intestine and large intestine and causes acute enteritis, vomiting, and watery diarrhea in pigs of all ages, especially in piglets. In particular, the damage is severe mainly in winter, from November to April, and it is known that the mortality rate of pre-weaning piglets within 1 week of birth is about 50%, and in severe cases, the mortality rate can reach almost 100% due to extreme dehydration.

The PED virus was first recognized in Europe in 1971, and G1a type PEDV CV777 was further identified and separated in Belgium in 1976. The virus had spread through Europe in 1980s, and the outbreaks have occurred in East Asian countries including China, Korea, Japan, Taiwan in 1990s. Further, G2b type PEDV, which is more virulent than the G1a type, had first emerged in China in 2010. The new type PEDV has spread to North America (the United State and Canada) and further to Southeast Asia and Europe, causing severe damage. In 2013, the damage was estimated to about 2.2 trillion won due to the loss of productivity in the US swine industry. In Korea, it is reported that an outbreak of PEDV annually occurs in 20 to 40% of pig farms, causing 6% of the total pigs to be killed. It is also reported that the infection rate of the vehicles entering and leaving slaughterhouses reaches about 60% (Korea Rural Economic Institute, Korea Swine Veterinary Association).

Until now, the only way to prevent the G2b type PED virus is by thorough sterilization. Many farms use an artificial infection method or the existing G1a type PEDV vaccine to prevent the damage caused by viral diseases, but there is a limitation in preventing the G2b type PEDV infection. In addition, the newly developed inactivated G2b type PEDV vaccine is also being used. However, several problems have been raised in regard to the preventive measures of PEDV, such as showing a limitation of the inactivated vaccine for the prevention of digestive diseases because the inactivated vaccines are only used instead of the development of live vaccines. In order to overcome such problems, development of agents for prevention and treatment of PED virus (vaccines etc.) and treatment (IgY, essential oil, organic acid, probiotics, etc.) is actively carried out. In particular, a method of enhancing immunity using a functional material that stimulates the immune system in vivo while having an antiviral effect has been recently studied.

Immunity is generally divided into innate immunity and adaptive immunity. Innate immunity is a system that instantly defends pathogen infection from the first line, acting directly on invaders (antigens) or inducing adaptive immunity. Adaptive immunity is a more complex and precise system that recognizes and removes invaders, or acts as a memory for the corresponding invaders, thereby providing more permanent immune functions compared to the innate immunity. Dendritic cells (DCs), macrophages, and natural killer cells, which are antigen-presenting cells related to innate immunity, directly serve innate immune functions and possess receptors that assist in activation of various types of T-cells, thereby secreting cytokines. Adaptive immunity is a secondary defense system against antigens that have entered the body, and is a specific immune response carried out by B lymphocytes and T lymphocytes. The immune responses controlled by antigen-activated T cells include a cytotoxic T cell response and a helper T cell response. The dendritic cells, macrophages, and natural killer cells related to the innate immunity also recognize foreign invasive substances and secrete various kinds of cytokines such as IL-12 and IL-4 to thereby induce a response that appropriately changes the immunity of the host animal, and thus may provide the immune defense mechanism in a suitable direction. Naive CD4 T cells, which act as precursors of T cells, are differentiated by key cytokines. For example, if IL-12 (interleukin-12) is present in a high concentration, CD4 T cells promote the differentiation of Th1 (T helper 1) cells, thereby inducing a CTL (cytotoxic T lymphocyte) response that eradicates intracellular pathogens, whereas, if IL-4 (interleukin-4) is present in a high concentration, they induce a response that specifically eradicates extracellular pathogens (antibody secretion of B cells). In addition, the above-enumerated immune cells respond in an appropriate manner to invaders that have entered the body through an elaborate and complex process, by secreting TGF-beta (Transforming growth factor Beta) and IL-10 to suppress excessive immune responses such as an inflammatory reaction, secreting TGF-beta to inhibit excessive immune response and thereby activates regulatory T cells, stimulating the production of antibodies by transforming B cells into plasma cells in response to the secretion of TGF-beta and IL-6 (interleukin-6), or inducing an immune response (Th17) to eradicate false autoimmunity and extracellular pathogens. However, such immune responses sometimes require an additional and appropriate immune enhancer due to imbalanced or poor immune responses.

DISCLOSURE

Technical Problem

The present inventors have completed the present disclosure by isolating and identifying microorganisms capable of activating the immune system while exhibiting an inhibitory activity against the above-mentioned virus, and confirming their activities.

Technical Solution

It is one object of the present disclosure to provide a composition including:

(a) a *Lactobacillus plantarum* CJLP475 strain deposited under Accession No. KCCM12287P; and (b) a *Lactobacillus plantarum* CJLP17 strain deposited under Accession No. KCCM12249P.

According to one embodiment of the present disclosure, the (a) and (b) may be in the form of a strain itself, a lysate thereof, a culture thereof, a concentrate thereof or a dried form thereof.

It is another object of the present disclosure to provide a feed or a feed additive including the aforementioned composition.

It is still another object of the present disclosure to provide a food including the aforementioned composition.

It is still further another object of the present disclosure to provide a cosmetic including the aforementioned composition.

It is still further another object of the present disclosure to provide a pharmaceutical including the aforementioned composition.

It is still further another object of the present disclosure to provide a method for enhancing immunity of a subject, including administering the aforementioned composition to a subject in need.

It is still further another object of the present disclosure to provide a method for preventing or treating a virus-infected disease of a subject, including administering the aforementioned composition to a subject in need.

It is still further another object of the present disclosure to provide the use of the composition for prevention or treatment of virus-infected disease.

Advantageous Effects

The composition of the present disclosure has high acid-resistance and bile-resistance and can thus be provided as a probiotic. The composition activates immune cells in vivo and thereby regulates immune functions, and particularly exhibits an excellent inhibitory activity against Porcine epidemic diarrhea virus (PEDV) infection. In addition, it can be found that when the composition of the present disclosure is orally administered to sows, and the piglets that have been delivered from the sows are challenged with PED virus, the mortality of the piglets can be remarkably reduced. Accordingly, the present disclosure can provide a composition having an antiviral activity against PED virus, an immunity-enhancing activity, and an effect of improving weight gain and reducing diarrhea incidence in livestock, and thus, the composition can be effectively used as a feed composition or a composition for feed additives, a food composition, a cosmetic composition or a pharmaceutical composition.

BRIEF DESCRIPTION OF DRAWINGS

FIG. 1 shows images of blood agar plate confirming no hemolytic activity of the *Lactobacillus plantarum* CJLP475 strain and the *Lactobacillus plantarum* CJLP17 strain.

FIG. 2 is a graph showing no cytotoxicity of the composition including the *Lactobacillus plantarum* CJLP475 strain and the *Lactobacillus plantarum* CJLP17 strain.

FIG. 3 shows microscopic images illustrating the inhibitory effect against PED virus infection by the composition including the *Lactobacillus plantarum* CJLP475 strain and the *Lactobacillus plantarum* CJLP17 strain.

FIG. 4 is a graph showing the rate of increase of vaccine-specific IgG antibodies in the serum of the sows fed with the composition including the *Lactobacillus plantarum* CJLP475 strain and the *Lactobacillus plantarum* CJLP17 strain.

FIG. 5 is a graph showing the rate of increase of vaccine-specific IgA antibodies in the serum of the sows fed with the composition including the *Lactobacillus plantarum* CJLP475 strain and the *Lactobacillus plantarum* CJLP17 strain.

FIG. 6 is a graph showing the neutralizing antibody titer in colostrum of the sows fed with the composition including the *Lactobacillus plantarum* CJLP475 strain and the *Lactobacillus plantarum* CJLP17 strain.

FIG. 7 is a graph showing the content of vaccine-specific IgG antibodies in piglet serum after a PED virus challenge in piglets born from the sows fed with the composition including the *Lactobacillus plantarum* CJLP475 strain and the *Lactobacillus plantarum* CJLP17 strain.

FIG. 8 is a graph showing the content of TGF-beta in piglet serum after a PED virus challenge in piglets born from the sows fed with the composition including the *Lactobacillus plantarum* CJLP475 strain and the *Lactobacillus plantarum* CJLP17 strain.

FIG. 9 is a graph showing the V/C ratio of piglet jejunum after a PED virus challenge in piglets born from the sows fed with the composition including the *Lactobacillus plantarum* CJLP475 strain and the *Lactobacillus plantarum* CJLP17 strain.

FIG. 10 is a graph showing a goblet cell density of piglet colon after a PED virus challenge in piglets born from the sows fed with the composition including the *Lactobacillus plantarum* CJLP475 strain and the *Lactobacillus plantarum* CJLP17 strain.

FIG. 11 is a graph showing the mean body temperature for 7 days after a PED virus challenge in piglets born from the sows fed with the composition including the *Lactobacillus plantarum* CJLP475 strain and the *Lactobacillus plantarum* CJLP17 strain.

FIG. 12 is a graph showing the diarrhea incidence for 7 days after a PED virus challenge in piglets born from the sows fed with the composition including the *Lactobacillus plantarum* CJLP475 strain and the *Lactobacillus plantarum* CJLP17 strain.

FIG. 13 is a graph showing the survival rate for 7 days after a PED virus challenge in piglets born from the sows fed with the composition including the *Lactobacillus plantarum* CJLP475 strain and the *Lactobacillus plantarum* CJLP17 strain.

DETAILED DESCRIPTION OF EMBODIMENTS

Hereinafter, the present disclosure will be described in more detail. Meanwhile, each description and embodiment disclosed herein can be applied to other descriptions and embodiments, respectively. That is, all combinations of various elements disclosed herein fall within the scope of the present disclosure. Further, the scope of the present disclosure is not limited by the specific description described below.

One aspect of the present disclosure to overcome the objects above, there is provided a composition including:

(a) a *Lactobacillus plantarum* CJLP475 strain deposited under Accession No. KCCM12287P; and (b) a *Lactobacillus plantarum* CJLP17 strain deposited under Accession No. KCCM12249P.

Specifically, the composition may have an antiviral, acid-resistance, bile-resistance, and an immune-enhancing activity.

As used herein, the term "*Lactobacillus*" is a microorganism of aerobic or facultative anaerobic gram-positive *bacillus* widely distributed in nature. The microorganisms belonging to the genus *Lactobacillus* include *Lactobacillus plantarum*, etc. The present inventors provide novel strains belonging to the *Lactobacillus plantarum*, which were deposited under Accession Nos. KCCM12287P and KCCM12249P, and are designated as "*Lactobacillus plantarum* CJLP475" and "*Lactobacillus plantarum* CJLP17", respectively. They correspond to a probiotic strain, are harmless to the human body and can be used without side effects.

As used herein, the term "probiotics" refers to live bacteria that enter the body and provide a healthy benefit. Most of the probiotics known so far have been consumed through fermented milk products made from lactic acid bacteria such as *Lactobacillus*. In recent years, however, probiotics are available on the market in the form of fermented milk, granules, powder and the like, containing some of the bacteria such as *Bifidobacterium* and *Enterococcus*, in addition to *Lactobacillus*. The *Lactobacillus plantarum* CJLP475 and the *Lactobacillus plantarum* CJLP17 of the present disclosure may also be used in the form of fermented milk, granules, powder and the like, but are not limited thereto.

As used herein, the term "acid-resistance" refers to the property of withstanding high acidity. If the probiotics are acid-resistant, they can be prevented from being degraded or damaged even when exposed to strong acidic conditions in the stomach, by consumption through various routes of administration including oral administration.

As used herein, the term "bile-resistance" refers to the resistance to digestive enzymes in the bile. The bile is made from the liver and stored in the gallbladder, and is a weak alkaline greenish brown liquid that helps the digestion of fat in the duodenum of the small intestines. It emulsifies fat to help digestion and absorption. The bile is one of the major causes of reducing the effect of probiotic administration as they act on probiotics ingested through various routes including oral administration and the like.

Specifically, among the compositions of the present disclosure, the *Lactobacillus plantarum* CJLP475 strain was isolated from soy sauce (i.e., a traditional fermented food), and the *Lactobacillus plantarum* CJLP17 strain was isolated from the feces and colostrum of sows and piglets in domestic farms where the PED virus had occurred. The morphological characteristics of the strains is that each strain is a gram-positive *bacillus*, and that the *Lactobacillus plantarum* CJLP475 strain is represented by 16s rDNA nucleotide sequence of SEQ ID NO: 1, and the *Lactobacillus plantarum* CJLP17 strain is represented by 16s rDNA nucleotide sequence of SEQ ID NO: 2. Each of the nucleotide sequences was analyzed and found to be about 99% homologous with *Lactobacillus plantarum*. Accordingly, the present inventors deposited the novel isolated *Lactobacillus plantarum* CJLP17 strain at the Korean Culture Center of Microorganisms, an International Depositary Authority, under Budapest Treaty on Apr. 13, 2018, with Accession No. KCCM12249P and the *Lactobacillus plantarum* CJLP475 strain at the Korean Culture Center of Microorganisms, an International Depositary Authority, under Budapest Treaty on Jul. 11, 2018, with Accession No. KCCM12287P.

In order to stably maintain the *Lactobacillus plantarum* CJLP475 strain and the *Lactobacillus plantarum* CJLP17 strain of the present disclosure for a long period of time, the strains may be stored by dissolving the cells in a storage solution prepared by mixing a certain amount of glycerol in water at $-70°$ C., or may be freeze-dried by suspending the cells in sterilized 10% skim milk, but are not limited thereto, and may be stored for a long time by various known methods.

The composition of the present disclosure may not exhibit a hemolytic activity against red blood cells. Hemolysis refers to the destruction of red blood cells and the release of hemoglobin to the surrounding area, and is an action by which the red blood cells are hemolyzed by enzymes produced from harmful bacteria in vivo. Therefore, even if the composition is administered in vivo, it may not cause hemolysis in the blood vessel.

In addition, the composition of the present disclosure may have a weak resistance or no resistance to antibiotics. The antibiotics may specifically be, but are not limited to, ampicillin, clindamycin, gentamicin, kanamycin, erythromycin, ampicillin/sulbactam, chloramphenicol, or streptomycin. Accordingly, even when the composition is used in pharmaceuticals, health functional foods, feed additives, or the like, it has no resistance to antibiotics, and thus, the possibility of causing relevant pharmacological effects or environmental problems is low.

The composition may enhance the activation of immune cells to increase secretion of cytokines, or may be administered in vivo to promote immune function.

As used herein, the term "immune cells" refer to all cells that play a role in immune function in vivo, and can be largely divided into T cells and B cells. The immune cells may include, but are not limited to, Th1 or Th2 cells. The composition of the present disclosure may have an activity to stimulate immune cells and thereby increase the secretion of cytokines such as IL-12, IL-10, or TGF-beta.

In viral diseases, which generally show a high mortality rate, necrosis of cells or tissues themselves due to the virus can lead to a secondary infection and septicemia induced by other bacteria, an inflammatory disease caused by an over-activated immune response, or appetite reduction and dehydration. Therefore, when the antiviral efficacy (relevant to Th1, Th2), which suppresses the viral infection, and the immune response (Th2, anti-inflammation), which regulates the secondary infection and the excessive inflammation reaction, are simultaneously enhanced, an effective prevention and treatment effect for viral diseases can be achieved. As such, a method for simultaneously enhancing Th1 and Th2 in regards to providing an immune-enhancing effect through probiotics is not known in the art, and such a method has been newly discovered by the present inventors. In addition, the composition of the present disclosure has an immunomodulatory ability to regulate the Th1/Th2 imbalance.

As used herein, the term "cytokine" refers to a glycoprotein used as a signal substance for controlling and stimulating a body defense system, and may be, for example, IL-12, IL-10, or TGF-beta, but is not limited thereto.

The composition may promote the growth of a subject or reduce diarrhea incidence upon administration to a subject.

As used herein, the term "subject" may refer to all animals including humans in which the immunity is weakened or likely to be weakened. For example, the subject may include animals excluding humans or including humans. The animal may include not only humans, but also all animals that need the above-mentioned efficacy to be revealed, and may specifically be mammals such as cows, horses, sheep, pigs, goats, camels, antelopes, dogs, cats, and the like, or alternatively, it may be a livestock or pet.

The above administration method is not particularly limited, but may be administered through various routes including an oral or parenteral route as long as it can reach the target tissues. Examples thereof may be an oral administration.

The composition may increase antibodies in the body. The immunity of a subject can be improved by increasing the secretion of the antibodies involved in the immune function. The composition may be administered to a subject, and the administration method is not particularly limited, but may be administered through various routes including an oral or parenteral route as long as it can reach the target tissues. Examples thereof may be an oral administration. The body may be a body fluid such as blood or colostrum, but is not limited thereto. The antibody may be an IgG, an IgA, or a neutralizing antibody, but is not limited thereto.

The composition, when administered to a subject, may enhance the immunity in the offspring born from the subject through the maternal antibody. The enhancement of the immunity may include an increase in the antibody or cytokine secretion, but is not limited thereto.

The composition, when administered to a subject, may alleviate the symptoms of viral infection in the offspring born from the subject. The virus may be porcine epidemic diarrhea virus (PEDV), and may include without limitation any virus, whose infection can be inhibited by the composition of the present disclosure. The alleviation of the symptoms may include, but is not limited to, alleviating the conditions of digestive organs, maintaining normal body temperature, reducing diarrhea, and increasing survival rate.

The composition may have an antiviral activity against the porcine epidemic diarrhea virus (PEDV).

As used herein, the term "anti-virus" refers to the property of inhibiting a viral infection. Probiotics cannot inactivate a virus themselves, but can increase the immunity of a virus-infected subject by an immunological activity, thereby allowing to resist the viral infection.

Porcine epidemic diarrhea virus is coronavirus that infects the cells lining of the small intestine of pigs, causing porcine epidemic diarrhea which induces severe diarrhea and dehydration. The virus may include any virus, whose infection can be inhibited by the composition of the present disclosure, without limitation.

The strains corresponding to (a) and (b), respectively, in the composition of the present disclosure may be in the form of a strain itself, a lysate thereof, a culture thereof, a concentrate thereof or a dried form thereof. When the strains are treated on a subject, the activity and infection of PED virus can be remarkably suppressed. Thus, the composition may be used as an antiviral composition against PED virus, or a pharmaceutical, a functional food composition, a quasi-drug composition or a feed composition for preventing or improving porcine epidemic diarrhea.

According to one embodiment of the present disclosure, the (a) and (b) in the composition of the present disclosure may be in the form of a strain itself, a lysate thereof, a culture thereof, a concentrate thereof, or a dried form thereof, but are not limited thereto. Further details regarding the composition can be made reference to the above description.

The strains of the present disclosure can be cultured by a conventional method for culturing *Lactobacillus* strains. As the medium, a natural medium or a synthetic medium can be used. As the carbon source of the medium, for example, glucose, sucrose, dextrin, glycerol, starch and the like may be used. As the nitrogen source, peptone, meat extracts, yeast extracts, dried yeasts, soybean, ammonium salts, nitrate, and other organic or inorganic nitrogen-containing compounds may be used, but is not limited thereto. As the inorganic salts included in the medium, magnesium, manganese, calcium, iron, potassium, and the like may be used, but is not limited thereto. Amino acids, vitamins, nucleic acids and related compounds may be added to the medium in addition to the carbon source, the nitrogen source and the components of the inorganic salt. The composition of the present disclosure may be cultured for 12 hours to 4 days in a temperature range of 20° C. to 40° C.

In the present disclosure, the culture broth may be referred to the composition after the completion of culture, and more specifically, the culture broth may or may not include cells. Therefore, the culture broth may include a culture supernatant, a composition from which a culture supernatant is removed, or a concentrated composition thereof. The composition of the culture broth may additionally contain not only components required for conventional culture of *Lactobacillus*, but also components that act synergistically to the growth of *Lactobacillus*, and the compositions thereof may be readily selected by those skilled in the art.

In addition, the strain may be in a liquid state or a dry state, and the drying method may include, but not limited to, air drying, natural drying, spray drying, and freeze drying.

The composition may be a complex preparation containing two types of strains, in which (a) a *Lactobacillus plantarum* CJLP475 strain deposited under Accession No. KCCM12287P; and (b) a *Lactobacillus plantarum* CJLP17 strain deposited under Accession No. KCCM12249P are contained at the same time. Accordingly, the composition may be merely composed of two types of strains corresponding to (a) and (b), lysates thereof, cultures thereof, concentrates thereof, or dry products thereof, but is not limited thereto. In this case, the two types of strains corresponding to the above (a) and (b) may not necessarily be in the same form in the composition, and may be in a combination of forms, if necessary, the (a) may be in the form of a strain itself, and (b) may be in the form of a lysate of the strain, but are not limited thereto.

In the composition, the concentration of the mixture of the *Lactobacillus plantarum* CJLP475 strain and the *Lactobacillus plantarum* CJLP17 strain may be, but is not limited to, $10^5$ CFU/mL to $10^{10}$ CFU/mL, $10^5$ CFU/mL to $10^9$ CFU/mL, $10^5$ CFU/mL to $10^8$ CFU/mL, $10^5$ CFU/mL to $10^7$ CFU/mL, $10^5$ CFU/mL to $10^6$ CFU/mL, $10^6$ CFU/mL to $10^{10}$ CFU/mL, $10^7$ CFU/mL to $10^{10}$ CFU/mL, $10^5$ CFU/mL to $10^{10}$ CFU/mL, $10^9$ CFU/mL to $10^{10}$ CFU/mL, $10^6$ CFU/mL to $10^9$ CFU/mL, $10^6$ CFU/mL to $10^8$ CFU/mL, $10^6$ CFU/mL to $10^7$ CFU/mL, $10^7$ CFU/mL to $10^9$ CFU/mL, $10^7$ CFU/mL to $10^8$ CFU/mL, or $10^8$ CFU/mL to $10^9$ CFU/mL.

The composition may further include a cryoprotectant or an excipient. The cryoprotectant or excipient may be a non-naturally occurring substance or a naturally occurring substance, but is not limited thereto. In another embodiment, the cryoprotectant or excipient may be a substance that does not naturally contact with the *Lactobacillus plantarum* CJLP475 strain and the *Lactobacillus plantarum* CJLP17 strain, or a substance that is not naturally contained simultaneously with the two strains, but is not limited thereto. In still another embodiment, the composition may further include at least one cryoprotectant selected from the group consisting of glycerol, trehalose, maltodextrin, skim milk powder and starch, and/or at least one excipient selected from the group consisting of glucose, dextrin and skim milk. The cryoprotectant of the present disclosure may be contained in an amount of 0.01% to 20% by weight and 0.01% to 10% by weight based on the total weight of the composition. Specifically, the glycerol may be contained in an amount of 5% to 20% by weight, the trehalose may be contained in an amount of 2% to 10% by weight, the maltodextrin may be contained in an amount of 2% to 10% by weight, the skim milk powder may be contained in an amount of 0.5% to 2% by weight, and the starch may be contained in an amount of 0.1% to 1% by weight in the composition. In addition, the excipient may be contained in an amount of 75% to 95% by weight or 85% to 95% by weight based on the total weight of the composition.

Further, the method for preparing the composition may include mixing the strains of Lactobacillus plantarum CJLP475 and the Lactobacillus plantarum CJLP17 themselves, a lysate thereof, a culture thereof, a concentrate thereof, or a dried product thereof with an additive. The additive may be the above-mentioned cryoprotectant or excipient.

The composition may be used for a food, a functional food, a feed, a feed additive, a cosmetic composition, or a pharmaceutical composition.

The composition may be used for enhancing immunity.

The composition may be used for providing an antiviral activity.

In another aspect, there is provided a probiotic composition including the composition of the present disclosure as an active ingredient.

Probiotics are fixed on the walls of the digestive tract in the intestines to prevent the establishment of harmful bacteria and inhibit the proliferation of viruses. In addition, the beneficial digestive enzymes produced by probiotics promote growth by facilitating the absorption and utilization of nutrients.

A method for preparing the probiotic composition may include preparing each of a composition including a Lactobacillus plantarum CJLP475 strain deposited under Accession No. KCCM12287P and a composition including a Lactobacillus plantarum CJLP17 strain deposited under Accession No. KCCM12249P; and mixing the composition including the CJLP475 strain and the composition including the CJLP17 strain.

In one embodiment, the preparation method may include adding an additive to at least one of the compositions above, such as the composition including the CJLP475 strain, the composition including the CJLP17 strain, or the probiotic composition In another embodiment, the additive may be a cryoprotectant, and the method may further include a freeze-drying step after adding the additive.

Herein, the bacteria in the freeze-dried composition may be in a live state.

In still another embodiment, the preparation method may include preparing a predetermined amount of the composition into a package after the mixing step.

Herein, in the packaging step, the composition may be prepared into a package such that the total amount of strains including the CJLP475 strain and the CJLP17 strain is $10^6$ CFU/g or more.

In still another aspect of the present disclosure, there is provided a feed or a feed additive including the composition.

The composition above is as described above. Specifically, the composition of the present disclosure may be added to a feed additive or a feed composition including the feed additive for the purpose of promoting growth, reducing diarrhea incidence, and inhibiting viral activity.

As used herein, the term "feed additive" refers to substances added to a feed for the purpose of providing various effects, such as supplementing nutrients and preventing weight loss, promoting digestibility of cellulose in the feed, improving milk quality, preventing reproductive disorders and improving pregnancy rate, and preventing a high-temperature stress during the summer season. The feed additive of the present disclosure belongs to a supplementary feed according to the Control of Livestock and Fish Feed Act and may further include mineral preparations such as sodium hydrogen carbonate, bentonite, magnesium oxide, complex minerals, and trace minerals including zinc, copper, cobalt, and selenium; vitamins such as carotene, vitamin E, vitamins A, D, E, nicotinic acid, and vitamin B complex; amino acid protective agents such as methionine and lysine; fatty acid protective agents such as fatty acid calcium; and live bacteria and yeast preparations such as probiotics (lactic acid bacteria), yeast culture, and fungus fermented product.

As used herein, the term "feed" refers to any natural or artificial diet, a single meal, or the like, or a component of the single meal, which an animal eats, ingests and digests or which is suitable for eating, ingestion, and digestion. The feed including the composition for preventing or treating a metabolic disease according to the present disclosure as an active ingredient may be prepared into various forms of feeds known in the art, and may specifically include a concentrated feed, a crude feed, and/or a specialty feed.

The subjects to be raised may include any organism that can ingest the feed of the present disclosure, and may include pigs for the purpose of the present disclosure.

The content of the composition in the feed composition according to the present disclosure may be properly controlled depending on the kind and age of a subject to be applied, application forms, desired effects, and the like. For example, the composition may be contained in an amount of 0.01% to 20% by weight, 0.01% to 15% by weight, 0.01% to 10% by weight, 0.01% to 5% by weight, 0.01% to 1% by weight, 1% to 20% by weight, 1% to 15% by weight, 1% to 10% by weight, 1% to 5% by weight, 5% to 20% by weight, 5% to 15% by weight, 5% to 10% by weight, 10% to 20% by weight, 10% to 15% by weight, or 15% to 20% by weight, but is not limited thereto.

For administration, the feed composition of the present disclosure may further include a mixture of one or more of an organic acid such as citric acid, fumaric acid, adipic acid, lactic acid, and the like; phosphate such as potassium phosphate, sodium phosphate, polyphosphate, and the like; and a natural antioxidant such as polyphenol, catechin, tocopherol, vitamin C, green tea extract, chitosan, tannic acid, and the like. If necessary, other typical additives such as an anti-influenza agent, a buffer, a bacteriostatic agent, and the like may be added. Further, a diluent, a dispersing agent, a surfactant, a binder or a lubricant may be additionally added to formulate the composition into an injectable preparation such as an aqueous solution, a suspension, an emulsion, and the like, a capsule, a granule, or a tablet.

Further, the feed composition of the present disclosure may be used together with a nutrient supplement, a growth accelerator, a digestion-absorption accelerator, and a prophylactic agent, in addition various auxiliaries such as amino acids, inorganic salts, vitamins, antioxidants, antifungal agents, antimicrobial agents, and the like, as auxiliary components, and the main ingredients including vegetable protein feeds such as pulverized or fragmented wheat, barley, corn, and the like, animal protein feeds such as blood meal, meat meal, fish meal, and the like, animal fat and vegetable fat.

When the feed composition of the present disclosure is used as a feed additive, the feed composition may be added either alone or in combination with other components, and may be appropriately used according to a conventional method. The feed composition may be prepared in the administration form of an immediate release or a sustained release formulation, in combination with a non-toxic, pharmaceutically acceptable carrier. The carrier may be a non-naturally occurring substance or a naturally occurring substance, but is not limited thereto. In another embodiment, the carrier may be a substance that does not naturally contact with the *Lactobacillus plantarum* CJLP475 strain and the *Lactobacillus plantarum* CJLP17 strain, or a substance that is not naturally contained simultaneously with the two strains, but is not limited thereto. The edible carrier may be corn starch, lactose, sucrose, or propylene glycol. A solid carrier may be in the administration form of tablets, powders, troches, and the like, and a liquid carrier may be in the administration form of syrups, liquid suspensions, emulsions, solutions, and the like. Further, the administration agent may include a preservative, a lubricant, a solution accelerator, or a stabilizer, and may also include other agents for improving inflammatory diseases and substances useful for the prevention of virus.

The feed composition according to the present disclosure may be mixed with a feed in an amount of about 10 g to 500 g, specifically 10 g to 100 g per 1 kg, based on the dry weight of the feed. After being completely mixed, the feed composition may be provided as mash, or may be further subjected to a pelletizing, extensification, or extrusion process, but is not limited thereto.

In still further another aspect of the present disclosure, there is provided a food or a functional food including the composition.

Specifically, the composition of the present disclosure may be added to food for the purpose of promoting growth, promoting immunity, reducing diarrhea incidence, and inhibiting viral activity. The composition is as described above. The food may include a sitologically acceptable carrier. The carrier may be a non-naturally occurring substance or a naturally occurring substance, but is not limited thereto. In another embodiment, the carrier may be a substance that does not naturally contact with the *Lactobacillus plantarum* CJLP475 strain and the *Lactobacillus plantarum* CJLP17 strain, or a substance that is not naturally contained simultaneously with the two strains, but is not limited thereto.

The food of the present disclosure includes all forms of functional foods, nutritional supplements, health foods and food additives, and these types of food may be prepared into various forms according to conventional methods.

When the composition is used as a food additive, the composition may be added either alone or used in combination with other foods or food ingredients, and may be appropriately used according to a conventional method. The amount of mixed active ingredients may appropriately be determined depending on the purpose of use (prevention, health, or therapeutic treatment). In general, at the time of preparing a food or drink, the composition is added in an amount of 0.0001% to 1% by weight, specifically 0.0001% to 0.1% by weight based on a raw material composition including the composition. However, in the case of long-term administration for health and hygiene purposes or for the purpose of controlling health, the amount may be less than the above-described range There is no particular limitation on the type of the food. Examples of foods to which the composition can be added include meats, sausages, bread, chocolates, candies, snacks, confectionaries, pizzas, instant noodles, other noodles, gums, dairy products including ice creams, various kinds of soup, beverages, teas, drinks, alcoholic drinks, vitamin complexes, and the like, and all health functional foods in the ordinary sense are included.

The health drink composition of the present disclosure may further contain, as additional components, various flavoring agents or natural carbohydrates, as in conventional drinks. The aforementioned natural carbohydrates may include monosaccharides such as glucose, fructose, and the like; disaccharides such as maltose, sucrose, and the like; polysaccharides such as dextrin, cyclodextrin, and the like; and sugar alcohols such as xylitol, sorbitol, erythritol, and the like. Natural sweetening agents such as thaumatin, a stevia extract, and the like; and synthetic sweetening agents such as saccharin, aspartame, and the like may be used as the sweetening agent. A ratio of the additional components may be in a range of 0.01 to 0.04 parts by weight, specifically 0.02 to 0.03 parts by weight based on 100 parts by weight of the composition of the present disclosure.

In addition to the aforementioned components, the composition of the present disclosure may contain various nutritional supplements, vitamins, electrolytes, flavoring agents, coloring agents, pectic acid and salts thereof, alginic acid and salts thereof, organic acids, protective colloidal thickening agents, pH control agents, stabilizing agents, preservatives, glycerin, alcohols, carbonating agents used in carbonated drinks, and the like. The ratio of such additives is not important, but is generally chosen in a range of 0.01 to 0.1 parts by weight, based on 100 parts by weight of the composition of the present disclosure. Moreover, the composition of the present disclosure may include pulp for preparing a natural fruit juice, a fruit juice drink or a vegetable drink. The ratio of such pulp is not important, but is generally chosen in a range of 0.01 to 10 parts by weight, based on 100 parts by weight of the composition of the present disclosure. Such components may be used alone or in combination.

In still further another aspect of the present disclosure, there is provided a cosmetic including the composition.

Specifically, the composition of the present disclosure has an anti-inflammatory effect and an antiviral activity-inhibiting effect through immunity stimulation, and thus can be used as a cosmetic. The composition is as described above.

When the composition according to the present disclosure is used as a cosmetic, the composition may be prepared into various cosmetics in the conventional formulations known in the field of cosmetics. Upon preparation into each formulation, it may be prepared by adding a carrier or an excipient which is acceptable and necessary in the manufacture of the cosmetics for each formulation. The carrier may be a non-naturally occurring substance or a naturally occurring substance, but is not limited thereto. In another embodiment, the carrier may be a substance that does not naturally contact with the *Lactobacillus plantarum* CJLP475 strain and the *Lactobacillus plantarum* CJLP17 strain, or a substance that is not naturally contained simultaneously with the two strains, but is not limited thereto.

In still further another aspect of the present disclosure, there is provided a pharmaceutical including the composition. Specifically, the composition of the present disclosure has an anti-inflammatory effect and an antiviral activity-inhibiting effect by promoting growth, reducing diarrhea incidence and stimulating immunity, and thus can be used as a pharmaceutical. The composition is as described above.

When the composition according to the present disclosure is used as a pharmaceutical, the composition may be prepared into a conventional pharmaceutical formulation known in the art. The pharmaceutical may specifically be prepared into formulations for oral administration such as liquids, suspensions, powder, granules, tablets, capsules, pills, or extracts. Upon preparation into each formulation, it may be prepared by adding a carrier or an excipient which is acceptable and necessary in the manufacture of the cosmetics for each formulation. The carrier may be a non-naturally occurring substance or a naturally occurring substance, but is not limited thereto. In another embodiment, the carrier may be a substance that does not naturally contact with the *Lactobacillus plantarum* CJLP475 strain and the *Lactobacillus plantarum* CJLP17 strain, or a substance that is not naturally contained simultaneously with the two strains, but is not limited thereto. Typically, when the composition is prepared into a formulation for oral administration, at least one carrier selected from a diluent, a lubricant, a binder, a disintegrating agent, a sweetener, a stabilizer and a preservative may be used, and at least one additive selected from a flavoring agent, a vitamin and an antioxidant may be used. Any pharmaceutically acceptable excipient or additive may be used. Specifically, it is possible to use lactose, corn starch, soybean oil, microcrystalline cellulose or mannitol as the diluent; magnesium stearate or talc as the lubricant; and polyvinyl pyrrolidone or hydroxypropyl cellulose as the binder. In addition, it is possible to use calcium carboxymethylcellulose, sodium starch glycolate, polacrilin potassium or crospovidone as the disintegrating agent; white sugar, fructose, sorbitol or aspartame as the sweetener; sodium carboxymethylcellulose, β-cyclodextrin, white wax or xanthan gum as the stabilizer; and methyl paraoxybenzoate, propyl paraoxybenzoate or potassium sorbate as the preservative.

In still further another aspect of the present disclosure, there is provided a step of administering the composition of the present disclosure to a subject. The composition and the subject are as described above.

The subject may exhibit the efficacy of the composition, i.e., immune-enhancing activity, antiviral activity, and the like, by the administration.

The dosage for the administration may be, but is not limited to, $10^6$ CFU/day or more, $10^7$ CFU/day or more, $10^8$ CFU/day or more, $10^9$ CFU/day or more, $10^{10}$ CFU/day or more or $10^{11}$ CFU/day or more based on the mixture of the *Lactobacillus plantarum* CJLP475 strain and the *Lactobacillus plantarum* CJLP17 strain.

In still further another aspect of the present disclosure, there is provided a method for enhancing immunity of a subject, including administering the composition to a subject in need. The composition and the subject are as described above.

As used therein, the term "administration" means introducing the composition of the present disclosure to a subject by any appropriate method, and the administration route of the composition may include various routes such as oral or parenteral administration as long as it can reach the target tissue.

In still further another aspect of the present disclosure, there is provided a method for preventing or treating virus-infected disease of a subject, including administering the composition to a subject in need. The composition and the subject are as described above.

As used herein, the term "prevention" or "preventing" means all actions that are intended to inhibit, suppress, or delay a virus-infected disease by administration of the composition of the present disclosure. Further, as used herein, the term "treatment" or "treating" means all actions that are intended to ameliorate or beneficially change a symptom of a virus-infected disease by administration of the composition of the present disclosure.

DETAILED DESCRIPTION OF EMBODIMENTS

Hereinafter, the present disclosure will be described in more detail by way of Examples. However, these Examples are given for illustrative purposes only, and the scope of the invention is not intended to be limited by these Examples.

Example 1: Separation and Selection of Strains 1-1. Sample Collection and Separation of *Lactobacillus Plantarum* CJLP475 Strain

*Lactobacillus plantarum* CJLP475 strains isolated from soy sauce were smeared on a solid MRS medium (Difco, USA) containing 1.5% agar and incubated at 37° C. for 24 hours. The strains isolated from each sample were purely isolated by transferring them to a fresh medium, and the thus-isolated strains were stored in a nutrient medium supplemented with 20% glycerol at −70° C. or below. As a result, a total of 1,552 strains were collected, and strains having excellent antiviral activity were selected through the following examples.

As a result of the 16S rDNA sequencing analysis, the *Lactobacillus plantarum* CJLP475 strain showed the highest homology (99.9%) with the *Lactobacillus plantarum* standard strain (NBRC1589, GenBank Accession Number AB326351) and thus was identified as *Lactobacillus plantarum* and named "*Lactobacillus plantarum* CJLP475", and deposited at the Korean Culture Center of Microorganisms, an International Depositary Authority, under Budapest Treaty on Jul. 11, 2018, with Accession No. KCCM12287P. The analyzed 16S rDNA nucleotide sequence of the *Lactobacillus plantarum* CJLP475 is represented by SEQ ID NO: 1.

Meanwhile, the *Lactobacillus plantarum* CJLP475 strain was found to be gram-positive as a result of the Gram staining. Further, in order to analyze the biochemical characteristics, sugar fermentation patterns of the strain were analyzed by the API 50 CHL system (biomerieux Vitek, Inc., France) (Table 1).

TABLE 1

Analysis of Sugar Fermentation Patterns of *Lactobacillus plantarum* CJLP475

| Name of strain | CJLP475 | Name of strain | CJLP475 |
|---|---|---|---|
| Control | − | Esculin | + |
| Glycerol | − | Salicin | + |
| Erythritol | − | Cellobiose | + |
| D-Arabinose | − | Maltose | + |
| L-Arabinose | + | Lactose | + |
| Ribose | + | Melibiose | + |
| D-Xylose | − | Saccharose | + |
| L-Xylose | − | Trehalose | + |
| Adonitol | − | Inulin | − |
| β Methyl-xyloside | − | Melezitose | + |
| Galactose | + | D-Raffinose | + |
| D-Glucose | + | Amidon | − |
| D-Fructose | + | Glycogen | − |
| D-Mannose | + | Xylitol | − |

TABLE 1-continued

Analysis of Sugar Fermentation Patterns
of *Lactobacillus plantarum* CJLP475

| Name of strain | CJLP475 | Name of strain | CJLP475 |
|---|---|---|---|
| L-sorbose | − | β-Gentiobiose | + |
| Rhamnose | + | D-Turanose | + |
| Dulcitol | − | D-Lyxose | − |
| Inositol | − | D-Tagatose | − |
| Mannitol | + | D-Fucose | − |
| Sorbitol | + | L-Fucose | − |
| α Methyl-D-mannoside | + | D-Arabitol | − |
| α Methyl-D-glucoside | − | L-Arabitol | − |
| N Acetyl glucosamine | + | Gluconate | + |
| Amygdaline | + | 2-ceto-gluconate | − |
| Arbutin | + | 5-ceto-gluconate | − |

+: Positive,
−: Negative 1-2. Sample Collection and Separation of *Lactobacillus Plantarum* CJLP17 Strain Samples of feces and colostrum of sows and piglets were collected from the domestic farms where chronic outbreaks of PED virus had occurred. The thus-collected samples were subjected to a serial dilution, smeared on a solid MRS and BHI medium, and incubated at 37° C. for 48 hours. The strains isolated from each sample were purely isolated by transferring them to a fresh medium, and the thus-isolated strains were stored in a nutrient medium supplemented with 20% glycerol at −70° C. or below. As a result, a total of 1,552 strains were collected, and strains having excellent antiviral activity were selected through the following examples. As a result of 16S rDNA sequencing analysis, the *Lactobacillus plantarum* CJLP17 strain showed the highest homology (99.9%) with the *Lactobacillus plantarum* standard strain (NBRC15891, GenBank Accession Number AB326351) and was thus identified as *Lactobacillus plantarum* and named "*Lactobacillus plantarum* CJLP17", and deposited at the Korean Culture Center of Microorganisms, an International Depositary Authority, under Budapest Treaty on Apr. 13, 2018, with Accession No. KCCM12249P. The analyzed 16S rDNA nucleotide sequence of *Lactobacillus plantarum* KCCM12249P is represented by SEQ ID NO: 2.

Meanwhile, the *Lactobacillus plantarum* CJLP17 strain was found to be gram-positive as a result of the Gram staining. Further, in order to analyze the biochemical characteristics, sugar fermentation patterns of the strain were analyzed by the API 50 CHL system (biomerieux Vitek, Inc., France) (Table 2).

TABLE 2

Analysis of Sugar Fermentation Patterns
of *Lactobacillus plantarum* CJLP17

| Name of strain | CJLP17 | Name of strain | CJLP17 |
|---|---|---|---|
| Control | − | Esculin | − |
| Glycerol | − | Salicin | + |
| Erythritol | − | Cellobiose | + |
| D-Arabinose | − | Maltose | + |
| L-Arabinose | + | Lactose | + |
| Ribose | + | Melibiose | + |
| D-Xylose | − | Saccharose | + |
| L-Xylose | − | Trehalose | + |
| Adonitol | − | Inulin | − |
| β Methyl-xyloside | − | Melezitose | + |
| Galactose | + | D-Raffinose | − |
| D-Glucose | + | Amidon | − |
| D-Fructose | + | Glycogen | − |

TABLE 2-continued

Analysis of Sugar Fermentation Patterns
of *Lactobacillus plantarum* CJLP17

| Name of strain | CJLP17 | Name of strain | CJLP17 |
|---|---|---|---|
| D-Mannose | + | Xylitol | − |
| L-sorbose | − | B-Gentiobiose | + |
| Rhamnose | − | D-Turanose | + |
| Dulcitol | − | D-Lyxose | − |
| Inositol | − | D-Tagatose | − |
| Mannitol | + | D-Fucose | − |
| Sorbitol | + | L-Fucose | − |
| α Methyl-D-mannoside | + | D-Arabitol | − |
| α Methyl-D-glucoside | − | L-Arabitol | − |
| N Acetyl glucosamine | + | Gluconate | + |
| Amygdaline | + | 2-ceto-gluconate | − |
| Arbutin | + | 5-ceto-gluconate | − |

+: Positive,
−: Negative

Example 2: Assessment of Acid-Resistance and Bile-Resistance of Strains

In order to select the strains that can be used as probiotics, acid-resistance and bile-resistance of the obtained strains were assessed.

An artificial gastric juice medium was prepared for the assessment of acid-resistance. More specifically, the artificial gastric juice medium was prepared by adding pepsin to a liquid MRS medium so as to adjust the pH to 2.5, followed by sterilization.

The strains of Example 1 were subjected to a static culture in a liquid MRS medium at 37° C. for 18 hours after the second subculture. 1% of the pre-incubated strains were inoculated to the artificial gastric juice medium and subjected to a static culture at 37° C., and the culture broth was sampled at 0 hour and 3 hours. The sampled culture broth was serial diluted and smeared on the solid MRS medium, and incubated at 37° C. for 48 hours to measure viable cell count.

An artificial bile medium was prepared for the assessment of bile-resistance. More specifically, the artificial bile medium was prepared by adding 0.5% oxgall((bull bile) to a liquid MRS medium, followed by sterilization.

The strains of Example 1 were subjected to a static culture in a liquid MRS medium at 37° C. for 18 hours after the second subculture. 1% of the pre-incubated strains were inoculated to the artificial bile medium and subjected to a static culture at 37° C., and the culture broth was sampled at 0 hour and 24 hours. The sampled culture broth was serial diluted and smeared on the solid MRS medium, and incubated at 37° C. for 48 hours to measure viable cell count.

Through the above assessments, the strains having the highest acid-resistance and bile-resistance were selected and designated as *Lactobacillus plantarum* CJLP475 and *Lactobacillus plantarum* CJLP17. In order to compare the acid-resistance and bile-resistance of the *Lactobacillus plantarum* CJLP475 strain and the *Lactobacillus plantarum* CJLP17 strain with those of the conventionally known strains, the acid-resistance and the bile-resistance of the *Lactobacillus plantarum* standard strain (KCCM12116) obtained from the Korean Culture Center of Microorganisms were assessed in the same manner as the above method.

TABLE 3

Acid-Resistance Assessment (Unit: CFU/mL)

| | 0 hr | 3 hrs |
|---|---|---|
| Lactobacillus plantarum CJLP17 (KCCM12249P) | $1.1 \times 10^6$ | $4.0 \times 10^6$ |
| Lactobacillus plantarum CJLP475 (KCCM12287P) | $1.1 \times 10^6$ | $1.1 \times 10^7$ |
| Lactobacillus plantarum (KCCM12116) | $2.3 \times 10^7$ | $1.3 \times 10^7$ |

TABLE 4

Bile-Resistance Assessment (Unit: CFU/mL)

| | 0 hr | 24 hrs |
|---|---|---|
| Lactobacillus plantarum CJLP17 (KCCM12249P) | $1.3 \times 10^6$ | $1.1 \times 10^7$ |
| Lactobacillus plantarum CJLP475 (KCCM12287P) | $1.3 \times 10^8$ | $1.1 \times 10^7$ |
| Lactobacillus plantarum (KCCM12116) | $2.1 \times 10^7$ | $1.6 \times 10^6$ |

According to Tables 3 and 4 above, the number of cells of the Lactobacillus plantarum standard strain (KCCM12116) in the artificial gastric juice medium and the artificial bile medium was decreased. As a result, it can be seen that not all commonly known Lactobacillus plantarum have acid-resistance and bile-resistance.

Meanwhile, in the acid-resistance assessment, the number of cells in the Lactobacillus plantarum CJLP475 strain and the Lactobacillus plantarum CJLP17 strain was rather increased, indicating that the strains have excellent acid-resistance.

In the bile-resistance assessment, the number of cells in the Lactobacillus plantarum CJLP17 strain was increased, and the Lactobacillus plantarum CJLP475 strain had a smaller decrease in the number of cells as compared with the Lactobacillus plantarum standard strain (KCCM12116), indicating that both strains have excellent bile-resistance.

In addition, since each strain has excellent acid-resistance and bile-resistance, it can be implied that the composition including both strains has excellent acid-resistance and bile-resistance.

Example 3: Assessment of Safety of Strains 3-1. Confirmation of Hemolytic Activity of Strains β-Hemolysis is a phenomenon in which phospholipids supplied by red blood cells are hydrolyzed by phospholipid enzymes produced from harmful bacteria, resulting in hemolysis of red blood cells. In order to determine the hemolytic activity of the Lactobacillus plantarum CJLP475 strain and the Lactobacillus plantarum CJLP17 strain, blood agar plates (sheep blood 5% agar, Hanilkomed, Korea) were used. Each strain was streaked into the prepared blood agar plates and incubated at 37° C. for 24 hours to confirm the hemolysis.

As a result, as shown in FIG. 1, it was confirmed that the Lactobacillus plantarum CJLP475 strain and the Lactobacillus plantarum CJLP17 strain did not show hemolysis. These results suggest that they do not act as harmful bacteria in vivo.

3-2. Assessment of Antibiotic Susceptibility

The Lactobacillus plantarum CJLP475 strain and the Lactobacillus plantarum CJLP17 strain were independently inoculated into a liquid MRS medium and subjected to a static culture at 37° C. for 24 hours. The thus-cultured bacteria were soaked in sterilized cotton swabs and smeared on a solid Mueller Hinton II medium (Difco), and then antibiotic discs were placed on the medium and incubated at 37° C. for 24 hours. Ampicillin, clindamycin, gentamicin, kanamycin, erythromycin, ampicillin/sulbactam, chloramphenicol, and streptomycin discs (Oxoid, UK) were used as antibiotic discs for the antibiotic test.

As a result of the antibiotic susceptibility test of the Lactobacillus plantarum CJLP475 strain and Lactobacillus plantarum CJLP17 strain, each strain was not resistant to the above antibiotics (Table 5). Therefore, it can be found that even if the Lactobacillus plantarum CJLP475 strain and the Lactobacillus plantarum CJLP17 strain are used in pharmaceuticals, health functional foods, feed additives, etc., problems that may arise with respect to the resistance and environmental problems are less likely to occur, considering that they have no resistance to antibiotics.

TABLE 5

Inhibition of Bacterial Growth According to Antibiotics

| | Radius of Growth Inhibition Area Centered Around Antibiotics (mm) | |
|---|---|---|
| Antibiotics | CJLP475 | CJLP17 |
| Amp10 (Ampicillin) | 7.5 | 7.5 |
| C30 (Clindamycin) | 7 | 7 |
| CN120 (Gentamicin) | 5 | 5 |
| K30 (Kanamycin) | 1.5 | 1.5 |
| E15 (Erythromycin) | 12 | 12 |
| SAM20 (Ampicillin/Sulbactam) | 7 | 7 |
| S10 (Chloramphenicol) | 3.5 | 3.5 |
| DA2 (Streptomycin) | 4.5 | 4.5 |

Example 4: Assessment of Cytotoxicity

In order to investigate the effect of the strains on the survival of cells, the MTS assay was carried out using (3-(4,5-dimethyl-2-yl)-5-(3-carboxymethoxyphenyl)-2-(4-sulfophenyl)-2H-tetrazolium, (promega, USA) to assess the level of cytotoxicity on IPEC-J2 cells (intestinal pig epithelium cells). Each cell was incubated on a 96-well cell culture plate and treated with a strain mixture, in which the Lactobacillus plantarum CJLP475 and Lactobacillus plantarum CJLP17 were mixed in a ratio of 1:1, at different concentrations from $10^5$ CFU/mL to $10^7$ CFU/mL. After 24 hours, the MTS solution was added to the cell culture broth, and the cells were incubated for 2 hours, and the cell survival rate (%) was calculated by measuring the absorbance at 490 nm with a microplate reader.

As a result, as shown in FIG. 2, when the cells were treated at three different concentrations, it was confirmed that cell death was hardly observed at concentrations of $10^7$ CFU/mL or below. Accordingly, it can be seen that the composition substantially shows no cytotoxicity at concentrations of $10^7$ CFU/mL or below.

Example 5: Inhibitory Effect Against Viral Infection

In order to measure the inhibitory effect of the composition including the Lactobacillus plantarum CJLP475 strain and the Lactobacillus plantarum CJLP17 strain against viral infection, porcine epidemic diarrhea virus (PEDV) was prepared. Specifically, the virus was proliferated in Vero cells (CCL-81, kidney epithelial cells extracted from *Chlorocebus*), and MEM (Eagle's Minimum Essential Medium, Gibco BRL, USA), heat-inactivated 10% FBS (fetal bovine serum, v/v) and 1% (v/v) penicillin/streptomycin were as the media for culturing Vero cells. The Vero cells were incubated as a monolayer, washed twice with the media, and then all the solutions were removed. The virus was mixed at 0.1 MOI (multiplicity of infection) level in FBS-free MEM containing trypsin treated with 5 μg/mL TPCK (N-tosyl-L-phenylalanine chloromethyl ketone), treated with a minimal volume of the prepared culture cells, and then incubated in a 37° C. cell incubator containing 5% $CO_2$ for 2 to 3 days.

The viral infection was determined by the formation of virus syncytia. When a virus syncytium was formed, the virus culture broth was collected within 3 to 6 hours, and the cells were removed using a centrifuge and stored at −80° C. For the calculation of the infection titer of the virus, the Vero cells were incubated in a 96-well plate at a density of $2\times10^4$ cell/0.1 mL, and the cells were washed with PBS. Subsequently, the cells were added with a culture broth, in which the virus was subjected to a 2-fold serial dilution, and incubated for 24 to 48 hours to confirm viral infection, and the virus titer was calculated by the Reed & Muench method.

In order to measure the inhibitory effect of the composition including the *Lactobacillus plantarum* CJLP475 strain and the *Lactobacillus plantarum* CJLP17 strain against viral infection, the composition, and peripheral blood mononuclear cells (PBMC) and lymphocytes in mesenteric lymph node (mLN) extracted from 21-day-old weaned piglets were reacted for 20 to 24 hours, and then independently treated on the 96-well cell culture plate, in which IPEC-J2 was incubated, and incubated in a 37° C. cell incubator containing 5% $CO_2$ for 2 to 4 hours. The PED virus (SM98 or KPEDV9) at a dose of 100 $TCID_{50}$/mL (50% of tissue cell infectious dose) was aliquoted to each plate and incubated for 48 hours. In order to confirm the viral infection, the cell culture plate was fixed with methanol after completion of the culture, stained with crystal violet, and then the wells in which the cells were denatured, were examined with a microscope, thereby confirming the viral infection.

TABLE 6

Inhibitory Effect against PED virus infection of *Lactobacillus plantarum* CJLP475, *Lactobacillus plantarum* CJLP17, and Mixture thereof by Activated Immune Cells

|  | mLN PEDV | PBMC PEDV |
| --- | --- | --- |
| Negative Control | − | − |
| CJLP475 | + | ++ |
| CJLP17 | + | ++ |
| CJLP17 and CJLP475 | ++ | ++ |

++: Complete Inhibition,
+: Partial Inhibition,
−: Infected

As a result, as shown in Table 6 and FIG. 3, when the composition including both the *Lactobacillus plantarum* CJLP475 strain and the *Lactobacillus plantarum* CJLP17 strain was treated together with porcine immune cells, it can be judged that the immune cells activated by the composition can inhibit PED virus infection in the intestinal pig epithelial cells (IPEC-J2).

Considering that the total number of strains for each of the three experimental groups (CJLP475, CJLP17, CJLP17 and CJLP475) in Table 6 were the same, the inhibitory effect of the composition including both the *Lactobacillus plantarum* CJLP475 strain and the *Lactobacillus plantarum* CJLP17 strain against PED virus infection was significantly superior compared to the inhibitory effect of the compositions including each of the CJLP475 strain and the CJLP17 strain against the PED virus infection.

Example 6: Confirmation of Effect on Immunity and Colostrum of Sows

Since the antiviral effect of the composition including the *Lactobacillus plantarum* CJLP475 strain and the *Lactobacillus plantarum* CJLP17 strain was confirmed in Example 5, an experiment was carried out in order to confirm the effect thereof on the immunity and colostrum of sows when the composition was fed to the sows, as follows: fifteen sows at 6 weeks before delivery in the same delivery period were selected randomly for each experimental group from the farms in which no PED virus had occurred. All of the sows used in the experiment were inoculated with the PED virus vaccine at 8 weeks and 3 weeks before delivery. The experiment was carried out in a total of two experimental groups, i.e., a control group in which no strain was fed and a group fed with the composition including the *Lactobacillus plantarum* CJLP475 strain and the *Lactobacillus plantarum* CJLP17 strain. The feed was given in the form of common crumble feeds without antibiotics, and water was given to be consumed freely. The *Lactobacillus plantarum* CJLP475 strain and *Lactobacillus plantarum* CJLP17 strain were produced in the form of freeze-dried powder and stored in a refrigerator, and then added on top of the feed when given to the sows so that each sow was fed with the composition in an amount of $10^{10}$ CFU or more per day. The sows were fed for a total of 6 weeks, and in order to confirm the effect of the strains on the immunity and colostrum of the sows, the increase rate of vaccine-specific IgG antibody and the increase rate of vaccine-specific IgA antibody in sow serum, and the neutralizing antibody titer in colostrum were measured, and the results are shown in FIGS. 4, 5, and 6, respectively.

As a result of the experiment, the compositions including the *Lactobacillus plantarum* CJLP475 strain and the *Lactobacillus plantarum* CJLP17 strain increased the vaccine-specific IgG and IgA in sow serum compared to the control group. Further, when the change in the neutralizing antibody titer in the colostrum during delivery according to the feeding of the composition was examined, it was confirmed that the composition including the *Lactobacillus plantarum* CJLP475 strain and the *Lactobacillus plantarum* CJLP17 strain showed a higher neutralizing antibody titer than the control group.

Example 7: Effect of Improving Immunity of Piglets According to Feeding of the Composition in Sows In order to confirm the effect of the composition including the *Lactobacillus plantarum* CJLP475 strain and the *Lactobacillus plantarum* CJLP17 strain on the immunity of piglets born from the sows fed with the composition, an experiment was carried out using sows as in Example 6, and further, blood was collected from the piglets born from the sows 4 days after given colostrum to carry out an immunological analysis using an IgG ELISA kit. FIG. 7 shows the effect of the composition feeding on the immunity of piglets born from the sows for a total of 6 weeks.

As a result, the content of vaccine-specific IgG in piglet serum was found to be higher in the group fed with the composition including the *Lactobacillus plantarum* CJLP475 strain and the *Lactobacillus plantarum* CJLP17 strain than in the control group (FIG. 7).

Such results indicate that the piglets received high vaccine-specific IgG from the colostrum of the sows and thus, it can be found that the immunity of the piglets can be improved by feeding the sows with the composition including the *Lactobacillus plantarum* CJLP475 strain and the *Lactobacillus plantarum* CJLP17 strain.

Example 8: Effect of Challenge Test on Piglets Born from Sows Fed with the Composition In order to confirm the effect on the mortality of piglets when the piglets born from the sows fed with composition including the *Lactobacillus plantarum* CJLP475 strain and the *Lactobacillus plantarum* CJLP17 strain were infected with PED virus, an experiment was carried out using sows as in Example 6. Since this experiment required a challenge test on piglets with PED virus, the experimental groups were minimized according to the advice of the institutional animal care and use committee, in such a manner that the experimental group containing the single strain was not tested and only the group containing the composition including the *Lactobacillus plantarum* CJLP475 strain and the *Lactobacillus plantarum* CJLP17 strain was tested.

Twenty 4-day-old piglets after delivery from the sows fed with the composition including the *Lactobacillus plantarum* CJLP475 strain and the *Lactobacillus plantarum* CJLP17 strain were selected for each treatment group and challenged with PED virus (PEDv QIAP 1401, 100 $LD_{50}$%/ml). The body temperature and diarrhea score were measured daily for a total of 7 days after the challenge (0-3, 0: normal stool, 1: pale stool, 2: normal diarrhea, 3: severe diarrhea). The piglets were given milk substitute and water to be consumed freely, and each piglet was fed with the composition including the *Lactobacillus plantarum* CJLP475 strain and the *Lactobacillus plantarum* CJLP17 strain in an amount of $1 \times 10^{10}$ CFU per day by mixing with the milk substitute. When the piglets died, an autopsy was performed, and the jejunum and colon were sampled, fixed with neutralized formalin, embedded by treating with paraffin, and microsectioned, and then the tissue sections were de-paraffinized and hydrated. After H & E staining, the ratio of the height of the villi and the depth of the crypts was measured to examine the V/C ratio. The number of goblet cells per $mm^2$ was confirmed by sampling the mucosa of the colon. In addition, blood was collected from each subject and the serum was separated therefrom to compare the degree of inflammation inhibition for each treatment group. In this regard, the level of TGF-beta, which is a typical inflammation-inhibiting factor, was measured using ELISA (R&D Systems, USA), and the results of the challenge test are shown in FIGS. 8 to 13.

TGF-beta in piglet serum was found to be higher in the composition-fed group than in the control group. Therefore, it was confirmed that the anti-inflammatory reaction was further activated in the group fed with the composition including the *Lactobacillus plantarum* CJLP475 strain and the *Lactobacillus plantarum* CJLP17 strain (FIG. 8).

The V/C ratio of the piglet jejunum was higher in the composition-fed group than in the control group, and thus it was confirmed that the removal of the villi by the virus was alleviated as compared with the control group (FIG. 9).

The goblet cells in the piglet colon were present in a higher content in the composition-fed group than the control group, and thus it was confirmed that the intestinal mucosa-forming inhibition caused by the PED virus infection was significantly reduced (FIG. 10).

As a result of examining the change in the body temperature of the piglets after PED virus challenge, it was confirmed that the body temperature was maintained within the normal range in the composition-fed group as compared to the control group. In particular, at 5, 6 and 7 dpi, the change in the body temperature of the piglets born from the sows fed with the composition significantly maintained the mean body temperature as compared to the control (FIG. 11).

As a result of confirming the diarrhea score (clinical significance score) of the piglet caused by the PED virus, the diarrhea score in the experimental group fed with the composition was significantly lower than that of the control group at 6 and 7 dpi (FIG. 12).

The survival rate of the piglets was observed until 7 days after the PED virus challenge. As a result, the survival rate of the control group was 55%, and the survival rate of the piglets born from the sows fed with PED virus was 65% when infected with PED virus, thereby showing more superior antiviral effect compared to the control group (FIG. 13).

Based on the above results, it was confirmed that the mortality rate of the piglets was reduced upon infection with the virus, because the immunity of the sows and the antibodies in the colostrum were improved by feeding the sows with the composition, and thus had an effect on the immunity of the piglets.

Example 9: Preparation of Probiotics Including *Lactobacillus plantarum* CJLP475 Strain and the *Lactobacillus plantarum* CJLP17 Strain The probiotic *Lactobacillus plantarum* CJLP475 strain and the probiotic *Lactobacillus plantarum* CJLP17 strain identified in Example 1 were produced on a mass-scale and freeze-dried to make probiotics suitable for use as a raw material of pharmaceuticals, foods, feeds, feed additives or cosmetics.

For production of each strain, each strain was incubated in a liquid MRS medium (Difco) at 37° C. for 18 hours while adjusting the pH to 6.0 with a 25% NaOH solution, followed by harvesting the strains by centrifugation. Each of the harvested strains was frozen at −40° C. with 5% dextrin and 10% skim milk serving as cryoprotectants, dried at 37° C. and powdered using a mixer. Each of the powdered live strains was mixed each other to adjust the number of strains to a desired level. The mixture was mixed with a suitable amount of an excipient such as glucose, lactose and skim milk for storage, and packaged in a sealable aluminum pouch.

The probiotics can be applied to various fields in accordance with a conventional method in the art, such as pharmaceuticals, foods, feeds, cosmetics and the like. For example, the prepared probiotics may be mixed with grain powder used as a raw material for feeds to be used as probiotics for feeds, may be mixed with an excipient or additive to be used as probiotics for pharmaceuticals in the form of tablets, capsules and for foods, or may be mixed in a predetermined amount with raw materials of cosmetics to be used as probiotics for cosmetics.

While the present disclosure has been described with reference to the particular illustrative embodiments, it will be understood by those skilled in the art to which the present disclosure pertains that the present disclosure may be

The invention claimed is:

1. A composition comprising:
   (a) a *Lactobacillus plantarum* CJLP475 strain deposited under Accession No. KCCM12287P;
   (b) a *Lactobacillus plantarum* CJLP17 strain deposited under Accession No. KCCM12249P; and
   (c) a cryoprotectant or an excipient, wherein the excipient is at least one selected from the group consisting of glucose, dextrin and skim milk.

2. The composition of claim 1, wherein the composition has an antiviral activity against porcine epidemic diarrhea virus (PEDV).

3. The composition of claim 1, wherein the composition enhances immunity of a subject to which the composition is administered.

4. The composition of claim 3, wherein the subject is a livestock or pet.

5. The composition of claim 1, wherein the composition increases antibodies in the body of a subject to which the composition is administered.

6. The composition of claim 1, wherein the composition enhances immunity of the offspring born from a subject to which the composition is administered.

7. The composition of claim 1, wherein the composition alleviates the symptoms of a viral infection in the offspring born from a subject to which the composition is administered.

8. The composition of claim 1, wherein (a) and (b) are in the form of a strain itself, a lysate thereof, a culture thereof, a concentrate thereof or a dried form thereof.

9. The composition of claim 1, wherein the cryoprotectant is at least one selected from the group consisting of glycerol, trehalose, maltodextrin, skim milk powder and starch.

10. The composition of claim 1, wherein the cryoprotectant and the excipient are non-naturally occurring substances.

11. The composition of claim 1, wherein the composition is a freeze-dried composition.

12. A method for enhancing immunity of a subject, comprising: administering the composition according to claim 1 to a subject.

13. A method for preventing or treating a virus-infected disease of a subject, comprising: administering the composition according to claim 1 to a subject.

* * * * *

SEQUENCE LISTING

<160> NUMBER OF SEQ ID NOS: 2

<210> SEQ ID NO 1
<211> LENGTH: 1454
<212> TYPE: DNA
<213> ORGANISM: Unknown
<220> FEATURE:
<223> OTHER INFORMATION: Lactobacillus plantarum CJLP475

<400> SEQUENCE: 1

| | | | | | | |
|---|---|---|---|---|---|---|
| acgaactctg | gtattgattg | gtgcttgcat | catgatttac | atttgagtga | gtggcgaact | 60 |
| ggtgagtaac | acgtgggaaa | cctgcccaga | agcggggat | aacacctgga | aacagatgct | 120 |
| aataccgcat | aacaacttgg | accgcatggt | ccgagtttga | aagatggctt | cggctatcac | 180 |
| ttttggatgg | tcccgcggcg | tattagctag | atggtggggt | aacggctcac | catggcaatg | 240 |
| atacgtagcc | gacctgagag | ggtaatcggc | cacattggga | ctgagacacg | gcccaaactc | 300 |
| ctacgggagg | cagcagtagg | gaatcttcca | caatggacga | aagtctgatg | gagcaacgcc | 360 |
| gcgtgagtga | agaagggttt | cggctcgtaa | aactctgttg | ttaaagaaga | acatatctga | 420 |
| gagtaactgt | tcaggtattg | acggtattta | accagaaagc | cacggctaac | tacgtgccag | 480 |
| cagccgcggt | aatacgtagg | tggcaagcgt | tgtccggatt | tattgggcgt | aaagcgagcg | 540 |
| caggcggttt | tttaagtctg | atgtgaaagc | cttcggctca | accgaagaag | tgcatcggaa | 600 |
| actgggaaac | ttgagtgcag | aagaggacag | tggaactcca | tgtgtagcgg | tgaaatgcgt | 660 |
| agatatatgg | aagaacacca | gtggcgaagg | cggctgtctg | gtctgtaact | gacgctgagg | 720 |
| ctcgaaagta | tgggtagcaa | acaggattag | ataccctggt | agtccatacc | gtaaacgatg | 780 |
| aatgctaagt | gttggagggt | ttccgccctt | cagtgctgca | gctaacgcat | taagcattcc | 840 |
| gcctggggag | tacggccgca | aggctgaaac | tcaaaggaat | tgacggggc | ccgcacaagc | 900 |
| ggtggagcat | gtggtttaat | tcgaagctac | gcgaagaacc | ttaccaggtc | ttgacatact | 960 |
| atgcaaatct | aagagattag | acgttccctt | cggggacatg | gatacaggtg | gtgcatggtt | 1020 |
| gtcgtcagct | cgtgtcgtga | gatgttgggt | taagtcccgc | aacgagcgca | acccttatta | 1080 |
| tcagttgcca | gcattaagtt | gggcactctg | gtgagactgc | cggtgacaaa | ccggaggaag | 1140 |
| gtggggatga | cgtcaaatca | tcatgcccct | tatgacctgg | gctacacacg | tgctacaatg | 1200 |
| gatggtacaa | cgagttgcga | actcgcgaga | gtaagctaat | ctcttaaagc | cattctcagt | 1260 |
| tcggattgta | ggctgcaact | cgcctacatg | aagtcggaat | cgctagtaat | cgcggatcag | 1320 |
| catgccgcgg | tgaatacgtt | cccgggcctt | gtacacaccg | cccgtcacac | catgagagtt | 1380 |
| tgtaacaccc | aaagtcggtg | gggtaacctt | ttaggaacca | gccgcctaag | gtgggacaga | 1440 |
| tgattagggt | gaag | | | | | 1454 |

<210> SEQ ID NO 2
<211> LENGTH: 1333
<212> TYPE: DNA
<213> ORGANISM: Unknown
<220> FEATURE:
<223> OTHER INFORMATION: Lactobacillus plantarum CJLP17

<400> SEQUENCE: 2

```
gacgggcggt gtgtacaagg cccgggaacg tattcaccgc ggcatgctga tccgcgatta    60
ctagcgattc cgacttcatg taggcgagtt gcagcctaca atccgaactg agaatggctt   120
taagagatta gcttactctc gcgagttcgc aactcgttgt accatccatt gtagcacgtg   180
tgtagcccag gtcataaggg gcatgatgat ttgacgtcat ccccaccttc ctccggtttg   240
tcaccggcag tctcaccaga gtgcccaact taatgctggc aactgataat aagggttgcg   300
ctcgttgcgg gacttaaccc aacatctcac gacacgagct gacgacaacc atgcaccacc   360
tgtatccatg tccccgaagg gaacgtctaa tctcttagat ttgcatagta tgtcaagacc   420
tggtaaggtt cttcgcgtag cttcgaatta aaccacatgc tccaccgctt gtgcgggccc   480
ccgtcaattc ctttgagttt cagccttgcg gccgtactcc ccaggcggaa tgcttaatgc   540
gttagctgca gcactgaagg gcggaaaccc tccaacactt agcattcatc gtttacggta   600
tggactacca gggtatctaa tcctgtttgc tacccatact ttcgagcctc agcgtcagtt   660
acagaccaga cagccgcctt cgccactggt gttcttccat atatctacgc atttcaccgc   720
tacacatgga gttccactgt cctcttctgc actcaagttt cccagtttcc gatgcacttc   780
ttcggttgag ccgaaggctt tcacatcaga cttaaaaaac cgcctgcgct cgctttacgc   840
ccaataaatc cggacaacgc ttgccaccta cgtattaccg cggctgctgg cacgtagtta   900
gccgtggctt tctggttaaa taccgtcaat acctgaacag ttactcttaa atatgttctt   960
ctttaacaac agagttttac gagccgaaac ccttcttcac tcacggggcg ttgctccatc  1020
agactttcgt ccattgtgga agattcccta ctgctgcctc ccgtaggagt ttgggccgtg  1080
tctcagtccc aatgtggccg attaccctct caggttggct acgtatcatt gccatggtga  1140
gccgttacct caccatctag ctaatacgcc gcgggaccat ccaaaagtga tagccgaagc  1200
catctttcaa actcggacca tgcggtccaa gttgttatgc ggtattagca tctgtttcca  1260
ggtgttatcc cccgcttctg ggcaggtttc ccacgtgtta ctcaccagtt cgccactcac  1320
tcaaatgtaa atc                                                     1333
```